US010245413B2

(12) United States Patent
Shimada et al.

(10) Patent No.: US 10,245,413 B2
(45) Date of Patent: Apr. 2, 2019

(54) DISTAL ACCESS ASPIRATION GUIDE CATHETER (75) Inventors: Lynn Shimada, Orange, CA (US); Seferino Torres, Santa Ana, CA (US); Brian Strauss, Trabuco Canyon, CA (US); Jeffrey Valko, San Clemente, CA (US)

(73) Assignee: COVIDIEN LP, Mansfield, MA (US)

( * ) Notice: Subject to any disclaimer, the term of this patent is extended or adjusted under 35 U.S.C. 154(b) by 955 days.

(21) Appl. No.: 13/878,890

(22) PCT Filed: Oct. 3, 2011

(86) PCT No.: PCT/US2011/054600
§ 371 (c)(1),
(2), (4) Date: Oct. 18, 2013

(87) PCT Pub. No.: WO2012/047803
PCT Pub. Date: Apr. 12, 2012

(65) Prior Publication Data
US 2014/0046297 A1    Feb. 13, 2014

Related U.S. Application Data

(60) Provisional application No. 61/389,688, filed on Oct. 4, 2010.

(51) Int. Cl.
*A61M 25/00* (2006.01)
*A61L 29/02* (2006.01)
(Continued)

(52) U.S. Cl.
CPC ....... *A61M 25/0053* (2013.01); *A61B 5/6852* (2013.01); *A61B 10/04* (2013.01);
(Continued)

(58) Field of Classification Search
CPC .......... A61M 25/0053; A61M 25/0045; A61M 25/005; A61M 25/0054; A61B 5/6852
See application file for complete search history.

(56) References Cited

U.S. PATENT DOCUMENTS 4,676,229 A   6/1987 Krasnicki et al.
4,955,862 A   9/1990 Sepetka
(Continued)

FOREIGN PATENT DOCUMENTS

CN   1258826 A   7/2000
EP   0523928 A2   1/1993
(Continued)

OTHER PUBLICATIONS

International Search Report for PCT/US2011/54600, dated Nov. 1, 2013, 3 pages.
(Continued)

*Primary Examiner* — Nathan R Price
*Assistant Examiner* — Melissa A Snyder
(74) *Attorney, Agent, or Firm* — Shumaker & Sieffert, P.A.

(57) ABSTRACT

Distal access aspiration guide catheter system and methods for delivering implantable devices, catheters, or substances in or near and/or restoring flow through body lumens, such as blood vessel lumens are described. A Distal access aspiration guide catheter having a proximal, medial, and distal possessing high flexibility, high resistance to kinking and a large lumen to wall thickness ratio.

39 Claims, 7 Drawing Sheets

US 10,245,413 B2
Page 2

(51) Int. Cl.
*A61L 29/06* (2006.01)
*A61L 29/08* (2006.01)
*A61L 29/12* (2006.01)
*A61B 5/00* (2006.01)
*A61B 10/04* (2006.01)
*A61B 17/32* (2006.01)
*A61M 25/10* (2013.01)

(52) U.S. Cl.
CPC ...... *A61B 17/320016* (2013.01); *A61L 29/02* (2013.01); *A61L 29/06* (2013.01); *A61L 29/085* (2013.01); *A61L 29/126* (2013.01); *A61M 25/005* (2013.01); *A61M 25/0012* (2013.01); *A61M 25/0045* (2013.01); *A61M 25/0054* (2013.01); *A61M 25/10* (2013.01); *A61M 2025/0059* (2013.01); *Y10T 29/49826* (2015.01); *Y10T 29/49865* (2015.01)

(56) References Cited

U.S. PATENT DOCUMENTS

| | | |
|---|---|---|
| 5,041,100 A | 8/1991 | Rowland et al. |
| 5,045,072 A | 9/1991 | Castillo et al. |
| 5,180,376 A | 1/1993 | Fischell |
| 5,279,596 A | 1/1994 | Castaneda et al. |
| 5,358,493 A | 10/1994 | Schweich, Jr. et al. |
| 5,380,304 A | 1/1995 | Parker |
| 5,405,338 A | 4/1995 | Kranys |
| 5,454,795 A * | 10/1995 | Samson ............... A61L 29/041 600/435 |
| 5,456,665 A | 10/1995 | Postell et al. |
| 5,484,425 A | 1/1996 | Fischell et al. |
| 5,538,512 A | 7/1996 | Zenzon et al. |
| 5,573,520 A | 11/1996 | Schwartz et al. |
| 5,658,264 A | 8/1997 | Samson |
| 5,662,622 A | 9/1997 | Gore et al. |
| 5,695,483 A | 12/1997 | Samson |
| 5,700,253 A | 12/1997 | Parker |
| 5,702,373 A * | 12/1997 | Samson ............... A61M 25/005 604/526 |
| 5,728,063 A | 3/1998 | Preissman et al. |
| 5,730,733 A | 3/1998 | Mortier et al. |
| 5,733,400 A | 3/1998 | Gore et al. |
| 5,795,341 A | 8/1998 | Samson |
| 5,827,201 A * | 10/1998 | Samson ............... A61M 25/09 600/585 |
| 5,853,400 A | 12/1998 | Samson |
| 5,876,386 A | 3/1999 | Samson |
| 5,879,499 A | 3/1999 | Corvi |
| 6,004,310 A | 12/1999 | Bardsley et al. |
| 6,022,341 A | 2/2000 | Lentz |
| 6,022,343 A | 2/2000 | Johnson et al. |
| 6,036,670 A | 3/2000 | Wijeratne et al. |
| 6,159,187 A | 12/2000 | Park et al. |
| 6,171,295 B1 | 1/2001 | Garabedian et al. |
| 6,186,978 B1 * | 2/2001 | Samson ............... A61M 25/005 604/525 |
| 6,193,705 B1 | 2/2001 | Molter et al. |
| 6,213,995 B1 | 4/2001 | Steen et al. |
| 6,254,588 B1 | 7/2001 | Jones et al. |
| 6,258,080 B1 | 7/2001 | Samson |
| 6,358,238 B1 | 3/2002 | Sherry |
| 6,368,315 B1 | 4/2002 | Gillis et al. |
| 6,368,316 B1 | 4/2002 | Jansen et al. |
| 6,436,090 B1 | 8/2002 | Sanchez et al. |
| 6,451,005 B1 | 9/2002 | Saitou et al. |
| 6,485,457 B1 | 11/2002 | Hisamatsu et al. |
| 6,503,223 B1 | 1/2003 | Sekido et al. |
| 6,589,227 B2 | 7/2003 | Sønderskov |
| 6,616,651 B1 | 9/2003 | Stevens |
| 6,673,102 B1 | 1/2004 | Vonesh et al. |
| 6,702,802 B1 | 3/2004 | Hancock et al. |
| 6,706,025 B2 | 3/2004 | Engelson et al. |
| 6,808,520 B1 | 10/2004 | Fourkas et al. |
| 6,991,626 B2 | 1/2006 | Wantink et al. |
| 7,001,369 B2 | 2/2006 | Griffin et al. |
| 7,540,865 B2 | 6/2009 | Griffin et al. |
| 7,704,245 B2 | 4/2010 | Dittman et al. |
| 7,794,448 B2 | 9/2010 | Grandt et al. |
| 7,846,148 B2 | 12/2010 | Zhou |
| 7,850,623 B2 * | 12/2010 | Griffin ............... A61M 25/0013 600/585 |
| 7,896,861 B2 | 3/2011 | McFerran et al. |
| 8,298,210 B2 | 10/2012 | Provost-Tine et al. |
| 8,926,560 B2 | 1/2015 | Dinh et al. |
| 2001/0027310 A1 | 10/2001 | Parisi et al. |
| 2002/0123738 A1 | 9/2002 | Jansen et al. |
| 2003/0028173 A1 | 2/2003 | Forsberg |
| 2003/0050686 A1 | 3/2003 | Raeder-Devens et al. |
| 2003/0135198 A1 | 7/2003 | Berhow et al. |
| 2005/0043713 A1 | 2/2005 | Zhou |
| 2005/0070879 A1 | 3/2005 | Coyle et al. |
| 2005/0070881 A1 | 3/2005 | Gribbons et al. |
| 2005/0234427 A1 | 10/2005 | Eder |
| 2006/0020256 A1 | 1/2006 | Bell et al. |
| 2006/0030835 A1 | 2/2006 | Sherman et al. |
| 2006/0135962 A1 | 6/2006 | Kick et al. |
| 2006/0135981 A1 | 6/2006 | Lenker et al. |
| 2006/0184106 A1 | 8/2006 | McDaniel et al. |
| 2006/0189896 A1 * | 8/2006 | Davis ............... A61M 25/0013 600/585 |
| 2006/0200074 A1 | 9/2006 | Zadno-Azizi |
| 2006/0200110 A1 | 9/2006 | Lentz et al. |
| 2006/0253102 A1 | 9/2006 | Nance et al. |
| 2006/0229589 A1 | 10/2006 | Itou et al. |
| 2007/0100285 A1 | 5/2007 | Griffin et al. |
| 2007/0135907 A1 | 6/2007 | Wilson et al. |
| 2007/0149951 A1 | 6/2007 | Wu et al. |
| 2008/0171952 A1 | 7/2008 | Mishima |
| 2008/0188832 A1 | 8/2008 | Tanioka et al. |
| 2008/0294118 A1 | 11/2008 | Chandrasekar et al. |
| 2008/0300577 A1 | 12/2008 | Trapp |
| 2009/0024110 A1 | 1/2009 | Heideman et al. |
| 2009/0030373 A1 | 1/2009 | Gill et al. |
| 2009/0166913 A1 | 7/2009 | Guo et al. |
| 2010/0145267 A1 | 6/2010 | Bishop et al. |
| 2011/0004147 A1 | 1/2011 | Renati et al. |
| 2011/0172643 A1 | 7/2011 | Jansen et al. |
| 2013/0172851 A1 | 7/2013 | Shimada et al. |

FOREIGN PATENT DOCUMENTS

| | | |
|---|---|---|
| EP | 1010440 A2 | 6/2000 |
| EP | 1092449 A1 | 4/2001 |
| EP | 1123714 A1 | 8/2001 |
| EP | 1955724 A1 | 8/2008 |
| JP | H11506369 A | 6/1999 |
| JP | 11-262529 | 9/1999 |
| JP | 2001129095 A | 5/2001 |
| JP | 2001-508670 | 7/2001 |
| JP | 2001190681 A | 7/2001 |
| JP | 2001218851 A | 8/2001 |
| JP | 2004357779 A | 12/2004 |
| JP | 2005525133 A | 8/2005 |
| JP | 2006288943 A | 10/2006 |
| JP | 2007029736 A | 2/2007 |
| JP | 2008-512196 | 4/2008 |
| JP | 2008188304 A | 8/2008 |
| JP | 2008531213 A | 8/2008 |
| JP | 2011083594 A | 4/2011 |
| JP | 2011514203 A | 5/2011 |
| WO | WO 97/44082 | 11/1997 |
| WO | 0003756 A1 | 1/2000 |
| WO | 03/013640 A1 | 2/2003 |
| WO | WO 2006/031582 A2 | 3/2006 |
| WO | 20061094135 A2 | 9/2006 |
| WO | WO-2009085486 A1 | 7/2009 |

(56) References Cited

FOREIGN PATENT DOCUMENTS

WO 2009111505 A1 9/2009
WO 2010068793 A1 6/2010

OTHER PUBLICATIONS

Office Action, and translation thereof, from counterpart Russian Patent Application No. 2013112656, dated Oct. 29, 2014, 10 pp.
Notification of the First Office Action, and translation thereof, from counterpart Chinese Patent Application No. 201180048038.0, dated Jan. 26, 2015, 23 pp.
Notice of Final Office Action, and translation thereof, from counterpart Japanese Patent Application No. 2013531952, dated Feb. 6, 2015, 6 pp.
International Search Report for PCT/US2012/045184, dated Oct. 4, 2012, 6 pages.
European Search Report for EP 12 18 5267, dated Feb. 28, 2013, 3 pages.
Notice of Last Preliminary Rejection, and translation thereof, from counterpart Korean Patent Application No. 10-2013-7008524, dated May 27, 2015, 15 pp.
Second Office Action, and translation thereof, from counterpart Chinese Application No. 201180048038.0, dated Aug. 18, 2015, 23 pp.
Search Report from counterpart European Patent Application No. 11831398.0, dated Oct. 20, 2014, 14 pp.
Notice of Reasons for Rejection, and translation thereof, from counterpart Japanese Patent Application No. 2013-531952, dated Apr. 15, 2014, 9 pp.
Notice of Preliminary Rejection, and translation thereof, from counterpart Korean Patent Application No. 10-2013-7008524, dated Jul. 24, 2014, 15 pp.
Third Office Action, and translation thereof, from counterpart Chinese Application No. 201180048038.0, dated Jan. 1, 2016, 6 pp.
Office Action from counterpart Canadian Application No. 2,813,067, dated Sep. 23, 2015, 3 pp.
Examiner's Report from counterpart Canadian Patent Application No. 2813067, dated Nov. 25, 2014, 3 pp.
U.S. Department of Health and Human Services, Class II Special Controls Guidance Document for Certain Percutaneous Transluminal Coronary Angioplasty (PTCA) Catheters, Center for Devices and Radiological Health, issued Sep. 8, 2010, 34 pp.
U.S. Department of Health and Human Services, "Guidance for Industry and FDA Staff—Non-Clinical Engineering Tests and Recommended Labeling for Intravascular Stents and Associated Delivery Systems," Center for Devices and Radiological Health, issued Apr. 18, 2010, 56 pp.
Prosecution History from U.S. Appl. No. 13/537,246, dated Aug. 13, 2014 through Jul. 29, 2016, 186 pp.
Non-Final Office Action from U.S. Appl. No. 13/537,246, dated May 19, 2017, 31 pp.
Notification of Reason for Rejection, and translation thereof, from counterpart Japanese Application No. 2015-114582, dated Apr. 3, 2017, 15 pp.
Final Office Action from U.S. Appl. No. 13/537,246, dated Mar. 7, 2017, 28 pp.
Response to Office Action dated May 19, 2017, from U.S. Appl. No. 13/537,246, filed Aug. 8, 2017, 20 pp.
Prosecution History from U.S. Appl. No. 13/623,941, dated May 9, 2014 through Dec. 5, 2014, 57 pp.
Communication pursuant to Article 94(3) EPC from counterpart European Patent Application No. 11831398.0, dated Mar. 9, 2018, 6 pp.
Final Office Action from U.S. Appl. No. 13/537,246, dated Nov. 17, 2017, 35 pp.
Notice of Final Rejection, and English translation thereof, from counterpart Japanese Patent Application No. 2015-114582, dated Dec. 18, 2017, 8 pp.
Pre-Appeal Brief Request for Review filed in U.S. Appl. No. 13/537,246, filed Jan. 8, 2018, 6 pp.
Notice of Allowance from U.S. Appl. No. 13/537,246, dated Jul. 13, 2018, 13 pp.
Response to Extended Search Report dated Mar. 9, 2018, from counterpart European Application No. 11831398.0, filed Jul. 10, 2018, 17 pp.
Response to Examination Report dated Feb. 7, 2014, from counterpart Canadian Application No. 2813067, filed Aug. 7, 2014, 14 pp.
Response to Examination Report dated Nov. 25, 2014, from counterpart Canadian Application No. 2813067, filed May 25, 2015, 19 pp.
Response to Examination Report dated Sep. 23, 2015, from counterpart Canadian Application No. 2813067, filed Mar. 23, 2016, 15 pp.
Response to Communication pursuant to Rules 70(2) and 70a(2) dated Nov. 6, 2014, from counterpart European Application No. 11831398.0, filed May 11, 2015, 29 pp.
First Office Action and Search Report, and translation thereof, from counterpart Chinese Application No. 201610566997.6, dated Oct. 31, 2018, 16 pp.
First Office Action and Examination Report, and English translation thereof, from counterpart Indian Application No. 2822/DELNP/2013, dated Nov. 27, 2018, 6 pp.

* cited by examiner

FIG. 1

Distal Access Catheter Aspiration Guide Catheter (Embodiment A)

| | Proximal Section | Medial Section | Distal Section |
|---|---|---|---|
| Tip Flexibility (Stiffness) | n/a | | A lateral flexibility of > 1000.degree./in-lb |
| Inner Diameter / Wall Thickness Ratio | Ratio 16 - 24:1 Preferably > 16:1 | Ratio 16 - 24:1 Preferably > 16:1 | Ratio 16 - 24:1 Preferably > 16:1 |
| Length 90-135 cm, Preferably 105 cm | | | |
| Inner Liner | 0.00025-0.001" Thick, PTFE, PFA, FEP, or other fluoropolymer Preferably PTFE 0.0005" thick | | |
| Metallic Kink Resistant Member | Proximal Section - Metallic 0.003" - 0.0125" Wide X 0.001"-0.005" Thick with 0.001" - 0.0125" Gap<br><br>Preferably Nitinol Type-1 (Fort Wayne Metals) 0.008" Wide X 0.0025" Thick with 0.002" gap | Medial Section - Metallic 0.003" - 0.0125" Wide X 0.001"-0.005" Thick with 0.001" - 0.0125" Gap<br><br>Preferably Nitinol Type-1 (Fort Wayne Metals, IN) 0.008" Wide X 0.0025" Thick with 0.004" gap | Distal Section - Metallic 0.003"-0.0125" Wide X 0.001"-0.005" Thick with 0.001" - 0.0125" Gap<br><br>Preferably Nitinol Type-1 (Fort Wayne Metals, IN) 0.008" Wide X 0.0025" Thick with 0.004" gap |
| Resin Kink Resistant Member | Resin Material thickness and width match the pitch described for the metallic kink resistant member.<br><br>Preferably Urethane Thermoset Resin Flexobond urethane adhesive, Bacon Industries Inc. MA | Resin Material thickness and width match the pitch described for the metallic kink resistant member.<br><br>Preferably Urethane Thermoset Resin Flexobond urethane adhesive, Bacon Industries Inc. MA | Resin Material thickness and width match the pitch described for the metallic kink resistant member.<br><br>Preferably Urethane Thermoset Resin Flexobond urethane adhesive, Bacon Industries Inc. MA |
| Outer Cover | Polymeric, .0005"-.002"<br><br>Preferably Polyester 0.001" Thick | Polymeric, .0005"-.002"<br><br>Preferably Polyester 0.005" Thick | Polymeric, .0005"-.002"<br><br>Preferably Polyolefin 0.0005" Thick (U4-140-CLR, from Cobalt Polymers, CA) |
| Hydrophilic Coating | PVP, Hylauronic Acid, etc. Distal Most 5-60 cm, preferably 40 cm | | |

Distal Access Aspiration Guide Catheter (Embodiment B)

| | Proximal Section | Medial Section | Distal Section A | Distal Section B |
|---|---|---|---|---|
| Tip Flexibility (Stiffness) | | | A lateral Flexibility of > 1000.degree./in-lb<br>Preferably of > 1500.degree./in-lb | A lateral Flexibility of > 1500.degree./in-lb<br>Preferably of > 2500.degree./in-lb |
| Wall Thickness / Inner Diameter Ratio | | | Ratio 16 - 24:1<br>Preferably > 16:1 | Ratio 16 - 24:1<br>Preferably > 16:1 |
| Length 90-135 cm, Preferably 105 cm | | | | |
| Inner Liner | | | 0.00025-0.001" Thick, , PTFE, PFA, FEP or other fluoropolymer<br>Preferably PTFE 0.0005" thick | |
| Metallic Kink Resistant Member | | Same as Embodiment A | Distal Section - Metallic<br>0.003" - 0.0125" Wide X 0.001"-0.005" Thick with 0.001" - 0.0125" Gap<br>*Preferably*<br>Nitinol Type-1 (Fort Wayne Metals, IN)<br>0.008" Wide X 0.0025" Thick with 0.004" gap | Distal Section - Metallic<br>0.003" - 0.0125" Wide X 0.001"-0.005" Thick with 0.001" - 0.0125" Gap<br>*Preferably*<br>Nitinol Type-1 (Fort Wayne Metals, IN)<br>0.004" Wide X 0.002" Thick with 0.002" gap |
| Resin Kink Resistant Member | | | Resin Material thickness and width match the pitch described for the metallic kink resistant member.<br>*Preferably*<br>Urethane Thermoset Resin Flexobond urethane adhesive, Bacon Industries Inc. MA | Resin Material thickness and width match the pitch described for the metallic kink resistant member.<br>*Preferably*<br>Urethane Thermoset Resin Flexobond urethane adhesive, Bacon Industries Inc. MA |
| Outer Cover | | | Polymeric, .0005"-.002"<br>*Preferably*<br>Polyolefin 0.0005" Thick (U4-140-CLR, from Cobalt Polymers, CA) | Polymeric, .0005"-.002"<br>*Preferably*<br>Polyolefin 0.0005" Thick (U4-140-CLR, from Cobalt Polymers, CA) |
| Hydrophilic Coating | | | Same as Embodiment A | |

Kink Resistance

ReFlex (Invention) Kink Radius - 0.174 +/- 0.008"
Penumbra Neuron - 0.250"

FIG. 4

ID to Wall Section Ratio

*Ratio 16 – 24:1*
*Preferably > 16:1*

*8F*
*Wall section 0.0045" - 0.0055"Preferably 0.005"ID – 0.094-0.096"*

*7F*
*Wall section 0.004" - 0.005"Preferably 0.0045"ID – 0.082-0.084"*

*6F*
*Wall section 0.003" - 0.004"Preferably 0.0035"ID – 0.072-0.073"*

*5F*
*Wall section 0.003"- 0.0035"Preferably 0.00325"ID – 0.059-0.060"*

*4F*
*Wall section 0.0025"- 0.003"Preferably 0.00275"ID – 0.046-0.047"*

FIG. 5

DISTAL ACCESS ASPIRATION GUIDE CATHETER

RELATED APPLICATION

This application is a national phase application of international application No. PCT/US11/054600 filed on Oct. 3, 2011 that claims priority to U.S. Provisional Patent Application No. 61/389,688 filed Oct. 4, 2010, the entire disclosures of which are expressly incorporated herein by reference.

FIELD OF THE INVENTION

The present invention relates generally to medical devices and methods and more particularly to catheter-based systems and methods useable for accessing, diagnosing, or treating defects in blood vessels, such as blood vessels of the brain.

BACKGROUND OF THE INVENTION

Pursuant to 37 CFR 1.71(e), this patent document contains material which is subject to copyright protection. The copyright owner has no objection to facsimile reproduction of the entire patent document or the patent disclosure, as it appears in the Patent and Trademark Office patent file or records, but otherwise reserves all copyright rights whatsoever.

Stroke is a common cause of death and disability. In the United States, approximately 700,000 patients suffer from stroke annually. Stroke is a syndrome characterized by the acute onset of a neurological deficit that persists for at least 24 hours, reflecting focal involvement of the central nervous system, and is the result of a disturbance of the cerebral circulation. Its incidence increases with age. Risk factors for stroke include systolic or diastolic hypertension, hypercholesterolemia, cigarette smoking, heavy alcohol consumption, and oral contraceptive use.

Hemorrhagic stroke accounts for 20% of the annual stroke population. Hemorrhagic stroke often occurs due to rupture of an aneurysm or arteriovenous malformation (AVM), causing bleeding into the brain tissue and resultant infarction of brain tissue. The remaining 80% of strokes are due to ischemia that occurs due to occlusion of a blood vessel that deprives brain tissue of oxygen-carrying blood. Ischemic strokes are often caused by emboli or pieces of thrombotic tissue that have dislodged and traveled from other body sites, or from the cerebral vessels themselves, to occlude in the narrow cerebral arteries more distally. When a patient presents with neurological symptoms and signs, which resolve completely within 1 hour, the term transient ischemic attack (TIA) is used. Etiologically, TIA, and ischemic stroke share the same pathophysiologic mechanisms and thus represent a continuum based on persistence of symptoms and extent of ischemic insult.

Emboli occasionally form around the valves of the heart or in the left atrial appendage during periods of irregular heart rhythm and then are dislodged and follow the blood flow into the distal regions of the body. Those emboli can pass to the brain and cause an embolic stroke. As will be discussed below, many such occlusions occur in the middle cerebral artery (MCA), although such is not the only site where emboli come to rest.

When a patient presents with neurological deficit, a diagnostic hypothesis for the cause of stroke can be generated based on the patient's history, a review of stroke risk factors, and a neurologic examination. If an ischemic event is suspected, a clinician can tentatively assess whether the patient has a cardiogenic source of emboli, large artery extracranial or intracranial disease, small artery intraparenchymal disease, or a hematologic or other systemic disorder. A head CT scan is often performed to determine whether the patient has suffered an ischemic or hemorrhagic insult. Blood would be present on the CT scan in subarachnoid hemorrhage, intraparenchymal hematoma, or intraventricular hemorrhage.

To reach these lesions or occlusions microcatheter and microguidewire must be employed, but often the column support of these microcatheters is not strong enough to navigate through the distal reaches of the neurovasculature to effectively treat these sites. Often guide catheters are employed to act as a conduit to help support microcatheter access. Traditional guide catheters designed for coronary or peripheral use (U.S. Pat. No. 5,180,376 & U.S. Pat. No. 5,484,425 Fischell, U.S. Pat. No. 5,045,072 Castillo, U.S. Pat. No. 5,279,596 Castaneda, U.S. Pat. No. 5,454,795 Samson and U.S. Pat. No. 5,733,400 Gold), typically are not positioned above the skull base and limit their effectiveness in supporting microcatheters in the distal cerebrovasculature. Newer distal access guide catheters have been developed which are slightly longer, thinner, a bit more flexible than the early generations, but are constructed with the same manufacturing techniques as described in U.S. Pat. No. 5,180,376 & U.S. Pat. No. 5,484,425 Fischell, U.S. Pat. No. 5,045,072 Castillo, U.S. Pat. No. 5,279,596 Castaneda, U.S. Pat. No. 5,454,795 Samson and U.S. Pat. No. 5,733,400 Gold, but have not solved the kinking problem (Neuron Penumbra Recall—Oct. 2, 2009).

SUMMARY OF THE INVENTION

In accordance with one aspect of the present invention, there is provided a catheter device comprising a tubular member, an inner liner and an outer cover. The tubular member has an inner lumen and an outer surface. The tubular member comprises a metal helix having a helical gap and a polymeric material disposed within the helical gap. The inner liner extends through the lumen of the tubular member and defines an inner lumen of the catheter. The outer covering is disposed on the outer surface of the tubular member. The dimension(s) of the metal helix and/or the width of the helical gap may be constant over the entire length of the catheter or may be varied to provide for regionalized differences in flexural properties and/or kink resistance. In some embodiments, the components of the catheter device may be sized and constructed such that a distal region of the catheter device has an inner diameter to wall thickness ratio of from about 16:1 to about 24:1 (in some embodiments preferably about 16:1) and the following properties: a) a lateral flexibility of greater than 1200 degree/in-lb and/or b) a kink radius of about 0.174 inch+/− 0.008 inch or less and/or a tensile strength of 22N UTS.

Further in accordance with the present invention, there is provided a method for manufacturing a catheter comprising the steps of: A) forming or obtaining a metal helix having a helical gap; B) causing polymeric material to be disposed within the helical gap such that the polymeric material and the metal helix, in combination, form a tubular member having an outer surface and a lumen; C) causing an inner liner to be disposed within the lumen of the tubular member; and D) causing an outer cover to be disposed on the outer surface of the tubular member. In some embodiments, the polymeric material may be a cast polyurethane material, such as a polyurethane adhesive.

Still further in accordance with the present invention, there is provided a method for treating or diagnosing a disorder in a human or animal subject, said method comprising the steps of A) inserting into the subject's vasculature a catheter device of the type described herein and B) delivering a substance or device through the lumen of the catheter device and using the substance or device to treat or diagnose the disorder. In some embodiments of this method, the catheter device may be advanced into a blood vessel located within the subject's skull or which carry blood to or from the brain. Examples of blood vessels into which the catheter devices of the present invention may be advanced include the carotid arteries, cerebral arteries, anterior cerebral artery, middle cerebral artery and posterior cerebral artery.

Still further in accordance with the invention there is provided a system useable for performing a therapeutic or diagnostic task at a location within the body of a human or animal subject, such system comprising a) distal access aspiration guide catheter that has a proximal portion, a distal portion, a lumen and a distal end opening, said catheter distal tip being highly kink resistant, flexible, and with an inner diameter to catheter wall ratio of greater than 16 with a lateral stiffness (Flexibility) of greater than 1200.degree./in-lb. and b) working devices that are advance-able though the lumen of the catheter and out of its distal opening, said working devices being useable to perform the therapeutic or diagnostic task. Examples of the types of working devices that may be used in this system include but are but are not limited to; i) devices for removing thrombus or other obstructive matter from body lumens and/or to the distal opening of the access aspiration guide catheter for aspiration, ii) flow restoration devices useable to facilitate flow of a fluid though or around an obstruction within a body lumen and iii) devices for deploying or delivering implants (e.g., implantable occlusion coils or implantable embolic devices) and/or iv) devices that temporarily occlude the lumen.

Still further in accordance with the invention, there is provided a method for performing a therapeutic or diagnostic task at a location within the body of a human or animal subject, such method comprising the steps of: a) inserting into the subject's body a catheter that has a proximal portion, a distal portion, a lumen and a distal end opening, said catheter being catheter distal tip being highly kink resistant, flexible, and with a catheter inner diameter to catheter wall ratio of greater than 16 with a lateral stiffness (Flexibility) of greater than 1200.degree./in-lb. b) positioning the distal end opening of the catheter distally in a desired body lumen and c) advancing a working device though the lumen of the catheter and out of its distal opening; and, using the working device to perform the therapeutic or diagnostic task. Examples of the types of working devices that may be used in this method include but are but are not limited to; i) devices for removing thrombus or other obstructive matter from body lumens and/or to the distal access aspiration guide catheter for aspiration, ii) flow restoration devices useable to facilitate flow of a fluid though or around an obstruction within a body lumen and iii) devices for deploying or delivering implants (e.g., implantable occlusion coils or implantable embolic devices) and/or iv) devices that temporary occlude the lumen.

Still further in accordance with the invention there is provided a method for removing obstructive matter from a body lumen, such method comprising the steps of: a) distal access aspiration guide catheter that has a proximal portion, a distal portion, a lumen and a distal end opening, said catheter distal tip being highly kink resistant, flexible, and with a inner diameter to catheter wall ratio of >16 and; b) positioning the catheter, such that its distal end opening is within a body lumen; c) moving obstructive matter through the distal end opening and into the lumen of the catheter; and d) removing the catheter along with the obstructive matter that has been moved into the lumen of the catheter. In some embodiments, negative pressure may be applied through the lumen of the catheter to aspirate obstructive matter through the distal end opening and into the lumen of the catheter. In some embodiments, Step C of the method may comprise advancing an obstructive matter moving device (e.g., an embolectomy or thrombectomy device) from the catheter and using the obstructive matter-moving device to move obstructive matter through the distal end opening and into the lumen of the catheter.

For purposes of summarizing the invention, certain aspects, embodiments, variations, details, elements, examples, advantages, and novel features of the inventions are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein. These and other objects and advantages of the present invention will be more apparent from the following detailed description taken in conjunction with the accompanying drawings.

BRIEF DESCRIPTION OF THE DRAWINGS AND OTHER APPENDICES

Appended to, and forming a part of, this provisional patent application are the following materials:

FIG. 1A is a table containing component information and specifications for the embodiment shown in FIG. 1.

FIG. 2A is a table containing component information and specifications for the embodiment shown in FIG. 2.

DETAILED DESCRIPTION AND EXAMPLES

The following detailed description and the accompanying drawings to which it refers are intended to describe some, but not necessarily all, examples or embodiments of the invention. The described embodiments are to be considered in all respects only as illustrative and not restrictive. The contents of this detailed description and the accompanying drawings do not limit the scope of the invention in any way.

As used herein, the terms proximal and distal refer to a direction or a position along a longitudinal axis of a catheter or medical instrument. Proximal refers to the end of the catheter or medical instrument closer to the operator, while distal refers to the end of the catheter or medical instrument closer to the patient. For example, a first point is proximal to a second point if it is closer to the operator end of the catheter or medical instrument than the second point. The measurement term French, abbreviated Fr or F, is defined as three times the diameter of a device as measured in mm. Thus, a 3 mm diameter catheter is 9 French in diameter.

There is provided in accordance with one aspect of the present invention, a method for accessing regions of the vasculature through tortuous anatomy. Such vasculature includes the cerebrovasculature wherein access to the circle of Willis and beyond is exceedingly difficult due to the carotid siphon or vertebral artery anatomy that must be traversed to reach such locations without undo trauma or vessel straightening. The method comprises the steps of providing a catheter having a proximal end, a distal end of the catheter is inserted into the artery, and the support is distally advanced. Negative pressure can be applied to the proximal end of the catheter or an affixed aspiration port, to draw the thromboembolic material into the distal section. Catheters and other instrumentation (Working devices) can be inserted through the distal access aspiration guide catheter within the vasculature to gain access to locations where flexibility, kink resistance, torqueability, and column strength are required.

Typical arteries may be, among other examples, the common carotid artery, the internal carotid artery, the carotid siphon, the circle of Willis, etc. Alternatively, the artery may be the middle cerebral artery or the anterior cerebral artery, or elsewhere in the brain.

The method may additionally comprise the steps of introducing oxygenated medium into the artery through the aspiration lumen, or infusing pharmaceutical agent into the artery through the aspiration lumen. The pharmaceutical agent may be a vasodilator such as nifedipine or nitroprusside. The pharmaceutical agent may alternatively comprise t-PA. The thromboembolic material may be located using intravascular ultrasound, or carotid Doppler imaging techniques.

In accordance with another aspect of the present invention, there is provided an intracranial aspiration catheter. In accordance with the present invention, there is provided a method of establishing a flow path through a catheter, positioned across a non-linear segment of vasculature.

In certain embodiments, the aspiration catheter can serve as an guide catheter for placement of the micro-catheter. The guide catheter is advanced to a target region in cooperation with a guidewire to allow for steering and manipulation through the vasculature. In an exemplary procedure, the guidewire and guide catheter are introduced into the vasculature at a site within a femoral or iliac artery. Using a Seldinger technique, or other percutaneous procedure, a hollow 18-Gauge needle can be introduced into a femoral artery via percutaneous procedure. A guidewire is next advanced through the hollow needle and into the arterial tree. The hollow needle is next removed and an introducer sheath is advanced into the arterial tree. The guide catheter is next advanced through the catheter introducer either through the same guidewire or through a larger guidewire suitable for aortic traverse. The guide catheter is advanced through the aortic arch, into a carotid artery, through the carotid siphon and into a region proximate the circle of Willis. The guide catheter, because of its flexibility and high kink resistance can easily inserted through tortuous anatomy beyond the carotid siphon or the vertebral and basilar arteries. Once properly placed, the guide catheter can be utilized as a large conduit for the insertion of other working devices. Because of its large inner diameter multiple devices can be inserted. The guide catheter can serve as an aspiration device and as a shield for retrieval of debris, thrombus, or other material from the vasculature.

The guide catheter is preferably terminated, at its proximal end, with a luer or hemostasis valve and optionally with a connector offering multiple access ports, each of which can be valved or be terminated with a stopcock, etc.

There is disclosed a distal access aspiration catheter 100 in accordance with one aspect of the present invention. Although primarily described in the context of distal access aspiration guide catheter with a single central lumen, catheters of the present invention can readily be modified to incorporate additional structures, such as permanent or removable column strength enhancing mandrels, two or more lumen such as to permit drug or irrigant infusion or radiation delivery or to supply inflation media to an inflatable balloon, or combinations of these features, as will be readily apparent to one of skill in the art in view of the disclosure herein. In addition, the present invention will be described primarily in the context of providing distal vascular access for other endovascular working devices and removing obstructive material from remote vasculature in the brain.

The catheters disclosed herein may readily be adapted for use throughout the body wherever it may be desirable to introduce a very flexible thin walled catheter and kink resistant, which provides a relatively large diameter aspiration or supported working channel. For example, catheter shafts in accordance with the present invention may be dimensioned for use throughout the coronary and peripheral vasculature, the gastrointestinal tract, the urethra, ureters, Fallopian tubes and other lumens and potential lumens, as well. The lumen structure of the present invention may also be used as a minimally invasive percutaneous tissue tract expander, such as for diagnostic or therapeutic access to a solid tissue target (e.g., breast biopsy or tissue excision).

Figure 1:
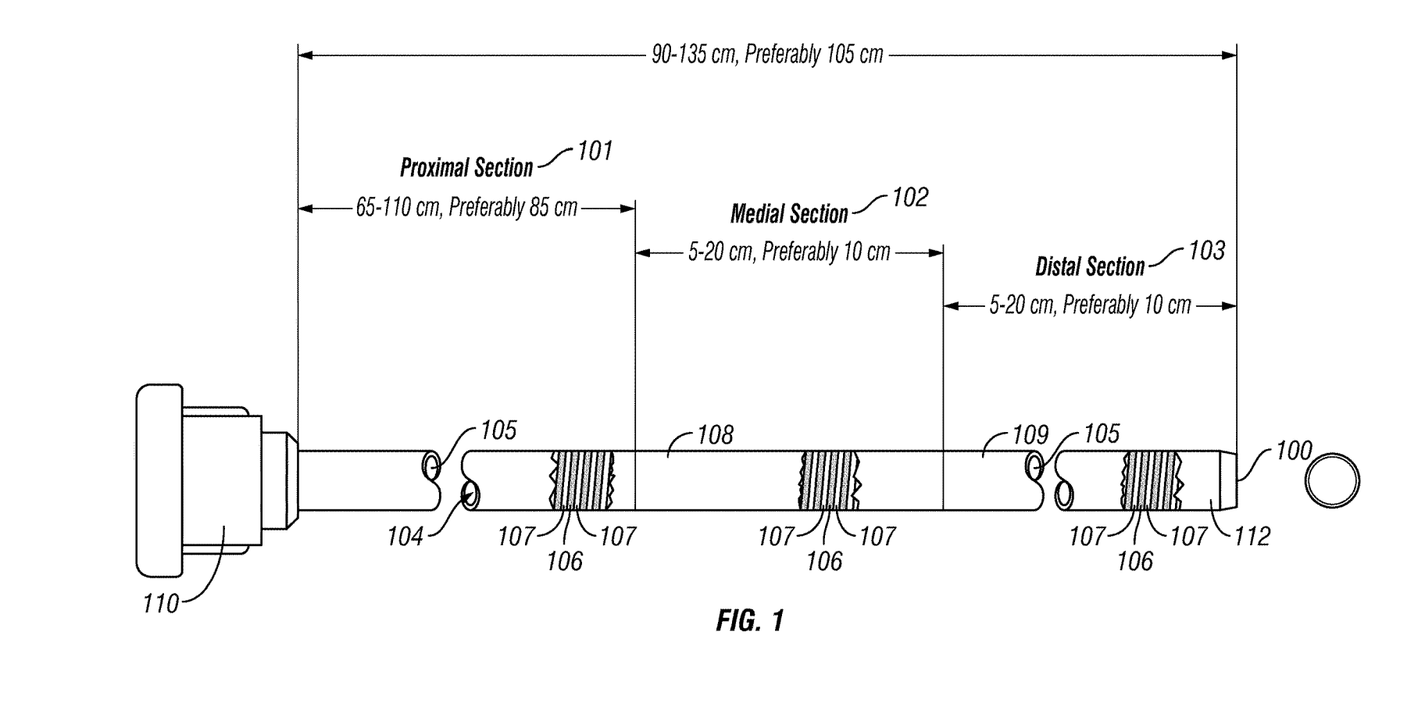
FIG. 1 is a side, partially cut-away view of one embodiment of a catheter device of the present invention having three sections.

FIG. 1 illustrates a side partial breakaway view of a guide catheter device 100. In this example, the guide catheter 100 comprises an elongate body having a proximal section 101, a medial section 102 and a distal section 103. A lumen 104 extends through the catheter 100. The elongate body of the catheter comprises an inner liner or sleeve 105, a first kink resistant member comprising a metallic helix 106, a second kink resistant member comprising a thermoset polymer material 107 is positioned within the helical gap of the metal helix 106, a distal outer cover 108 disposed on the distal section 103 and a proximal tubular cover 109 disposed on the proximal and medial sections. A luer or manifold 110 is provided on the proximal end of the elongate catheter body. Optionally, one or more radiographic marker(s) 112 may be positioned on or in the elongate catheter body, such as at the distal tip as shown in the example of FIG. 1. Certain specification and details of the catheter 100 shown in FIG. 1 are set forth in the table of FIG. 1A.

The polymers comprising the proximal tubular cover 108 and the distal tubular cover 109 are heat set using heat shrink tubing or other compression methodology and heat, such as that generated by a heated air flow source, radiant heat source, induction heater, radiofrequency heater, or the like. The metallic kink resistant member reinforcement 106 is a metallic structure, either of ribbon or flattened wire. The winds (i.e., helical convolutions) of the metallic kink resistant member 106 are disposed such that distributed flexibility can be generated a long the lengths of the catheter shaft. The helical gap within the metallic winds along with the thermoset set polymeric kink resistant member 107, can cause the flexibility to be substantially evenly distributed, or directed along a specific axis. The metal used in the metallic kink resistant member can be nitinol, stainless steel, cobalt-nickel alloy, titanium, or the like. The thermoset polymeric kink resistant member 107 may be thermoset urethane, or the like.

The kink resistant members 106 and 107 can beneficially be created such that the reinforcement becomes more flexible moving distally by changing the gap or thicknesses of these members. Additionally the flexibility can also be adjusted be changing the thicknesses and materials of the inner sleeve and outer tubular cover.

The proximal end of the catheter is additionally provided with luer or a manifold having one or more access ports as is known in the art. Generally, the manifold is provided with a guidewire port in an over-the-wire construction, an aspiration port, and a catheter insertion port. One or more of these features can be embodied within a single port. Alternatively, the aspiration port may be omitted if the procedure involves removal of the guidewire proximally from the guidewire port following placement of the aspiration catheter, and aspiration through the guidewire port. Additional access ports may be provided as needed, depending upon the functional capabilities of the catheter. The manifold may be injection molded from any of a variety of medical grade plastics, or formed in accordance with other techniques known in the art.

The proximal body segment will exhibit sufficient column strength to permit axial positioning of the catheter through a patient's vasculature. The catheter body may further comprise other components, such as radiopaque fillers; colorants; reinforcing materials; reinforcement layers, such as braids and helical reinforcement elements; or the like. In particular, the proximal body segment may be reinforced in order to enhance its column strength and torqueability while preferably limiting its wall thickness and outside diameter.

When present, an optional radiographic marker 112 will typically be provided at least at the distal end of the catheter 100. Other radiopaque markers may be provided elsewhere, such as on the support coil, if it is not already radiopaque. One embodiment of a radiopaque marker that may be used comprises a metal band, which is fully recessed within the distal end of the proximal body segment. Suitable marker bands can be produced from a variety of materials, including platinum, gold, and tungsten/rhenium alloy. Preferably, the radiopaque metal band will be recessed in an annular channel formed at the distal end of the proximal body segment.

Diameters outside of the preferred ranges may also be used, provided that the functional consequences of the diameter are acceptable for the intended purpose of the catheter. For example, the lower limit of the diameter for any portion of tubular body in a given application will be a function of the number of fluid or other functional lumen contained in the catheter, together with the acceptable minimum aspiration flow rate and collapse resistance.

Tubular body must have sufficient structural integrity (e.g., column strength or "pushability") to permit the catheter to be advanced to distal locations without buckling or undesirable bending of the tubular body. The ability of the body to transmit torque may also be desirable, such as to avoid kinking upon rotation, to assist in steering. The tubular body, and particularly the distal section, may be provided with any of a variety of torque and/or column strength enhancing structures. For example, axially extending stiffening wires, spiral wrapped support layers, braided or woven reinforcement filaments may be built into or layered on the tubular body.

In many applications, the proximal section will not be required to traverse particularly low profile or tortuous arteries. For coronary vascular applications, for example, the proximal section will be mostly or entirely within the relatively large diameter guide catheter. The transition can be located on the catheter shaft to correspond approximately with the distal end of the guide catheter when the balloon and/or distal end is at the treatment site. For certain other applications, such as intracranial catheterizations, the distal section is preferably at least about 5 cm long and small enough in diameter to pass through vessels as small as 3 mm or 2 mm or smaller. Catheters for this application may have a proximal section length of between about 60 cm to about 150 cm and a distal section length of between about 5 cm to about 15 cm, and the distal section is able to track a tortuous path of at least about 5 cm through vessels of less than about 3 mm lumen ID.

Figure 2:
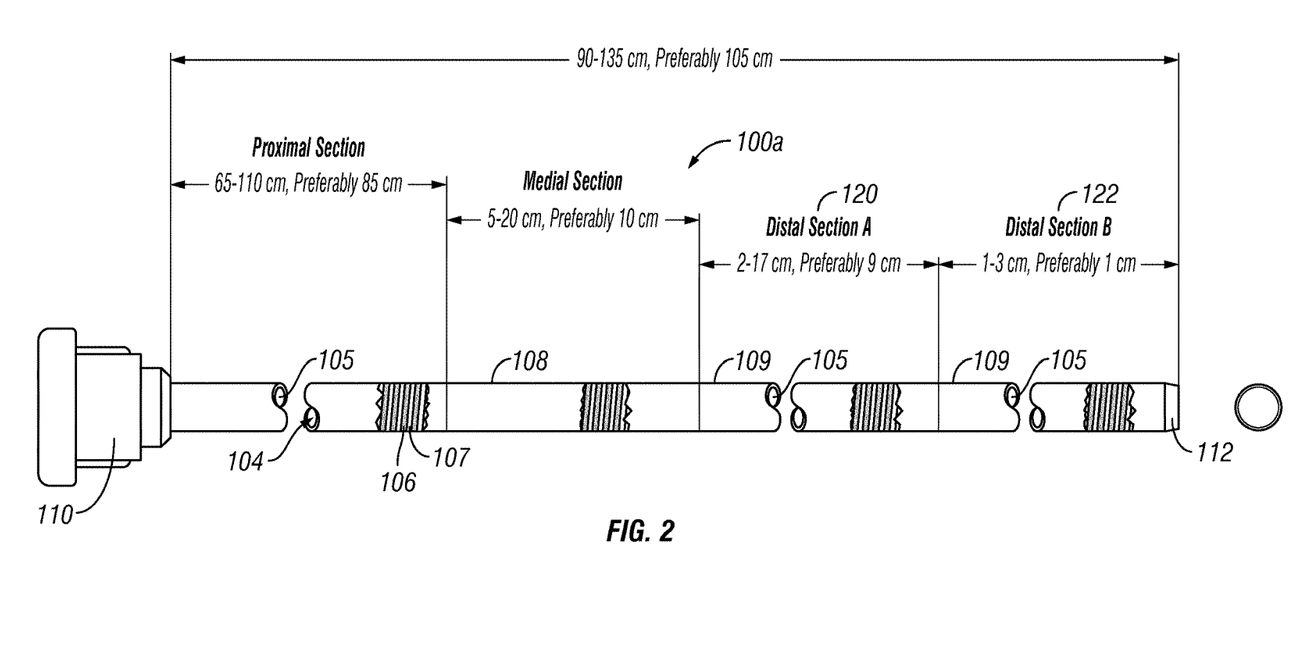
FIG. 2 is a side, partially cut-away view of one embodiment of a catheter device of the present invention having four sections.

The number of sections may vary. For example, FIG. 2 shows another embodiment of a catheter device 100a having essentially the same components and construction described above with respect to the catheter of FIG. 1, except that this catheter 100a has a first distal section 120 and a second distal section 122. The dimensions (e.g., width, thickness) of the metal helix 106 and/or the outer cover 109 may vary between the two distal sections 120, 122, thereby causing them to have different properties. Specific examples of those dimensions and other specifications for this catheter 100a are shown in the table of FIG. 2A.

Figure 3:
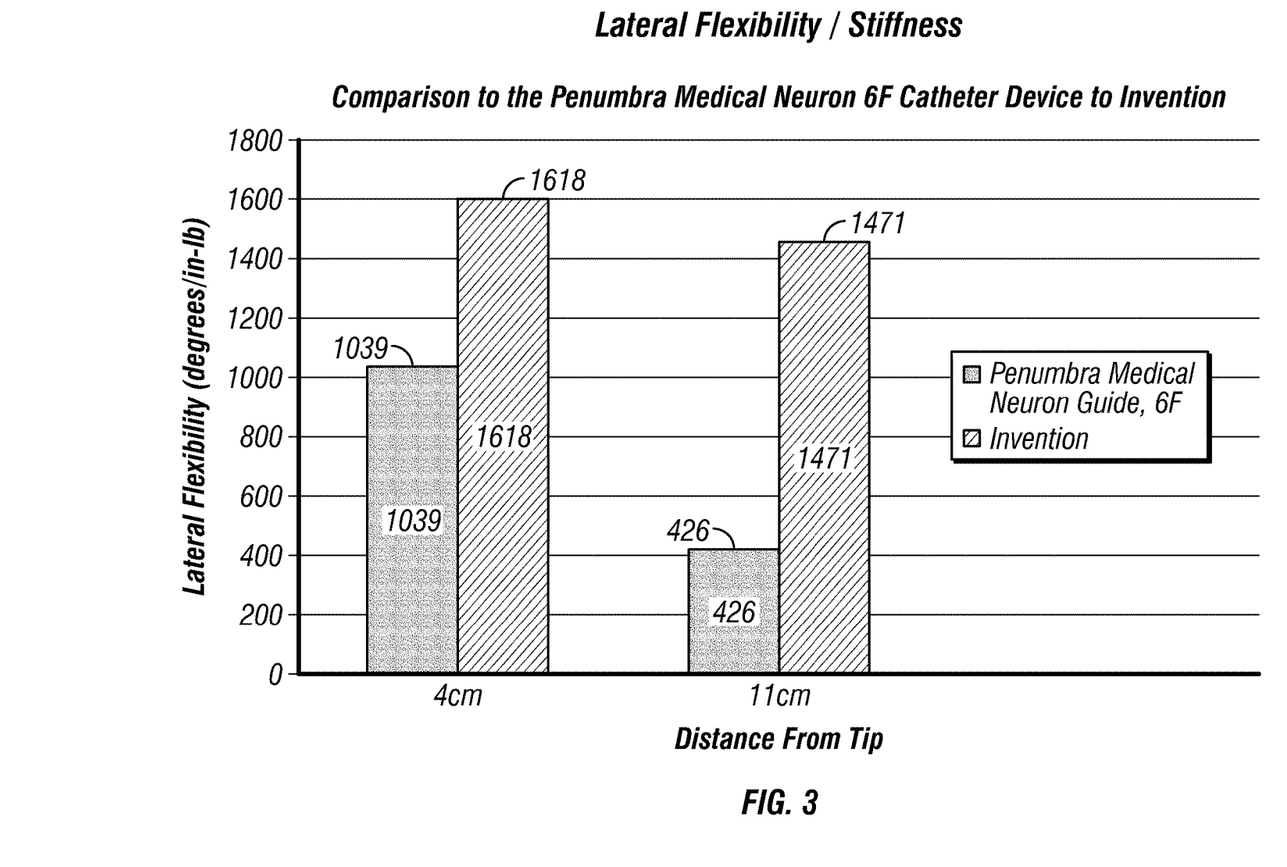
FIG. 3 is a bar graph comparing lateral flexibility/stiffness of a catheter 100 of the present invention (as seen in FIG. 1) with a another guide catheter device.

FIG. 3 is a bar graph comparing lateral flexibility/stiffness of a catheter 100 of the present invention (as seen in FIG. 1) with a another guide catheter device.

Figure 4:
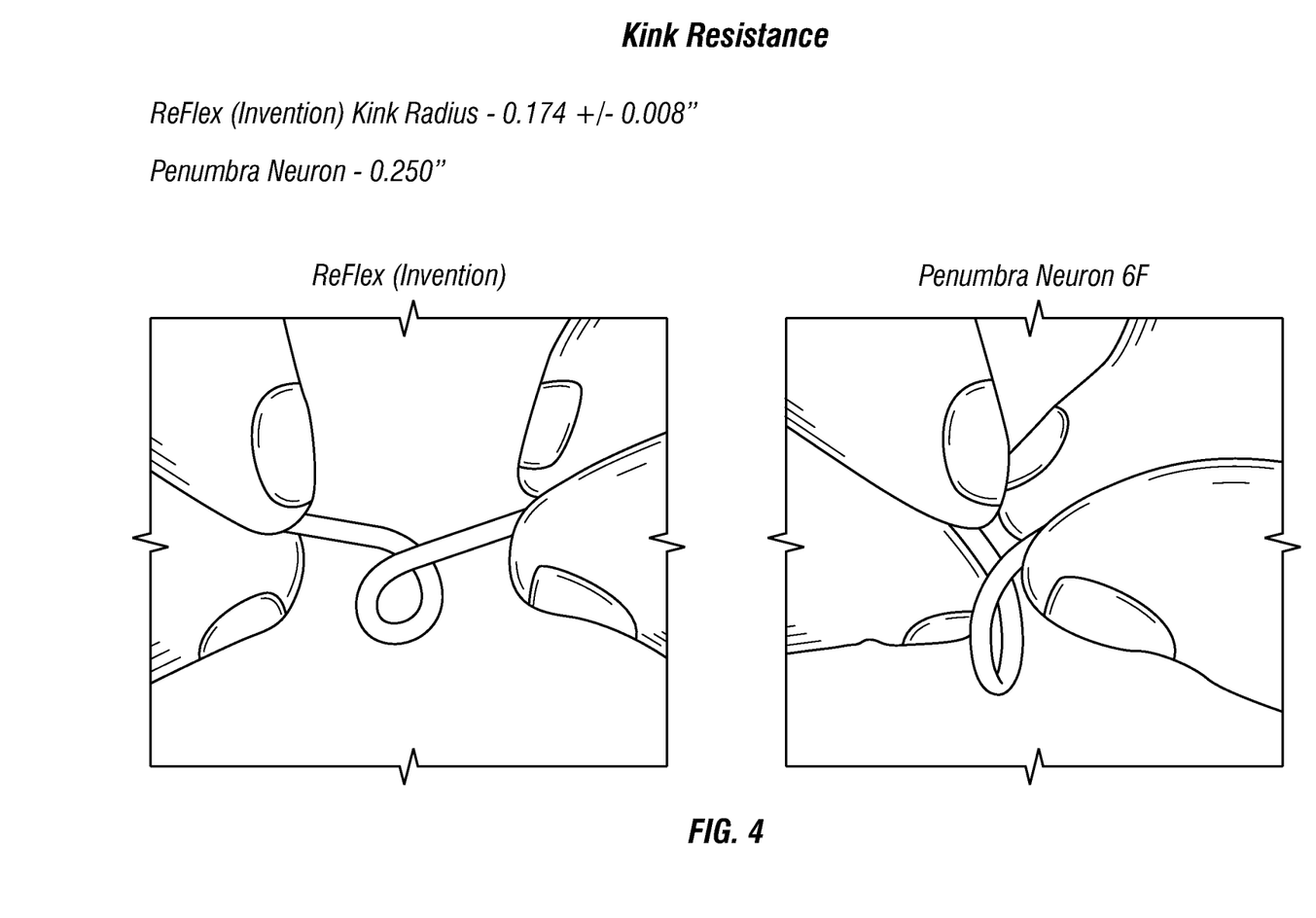
FIG. 4 is a pictorial comparison illustrating the kink resistance of a catheter 100 of the present invention (as seen in FIG. 1) with a another guide catheter device.

FIG. 4 shows photographs and data comparing kink resistance of a catheter 100 of the present invention (as seen in FIG. 1) with a another guide catheter device.

Figure 5:
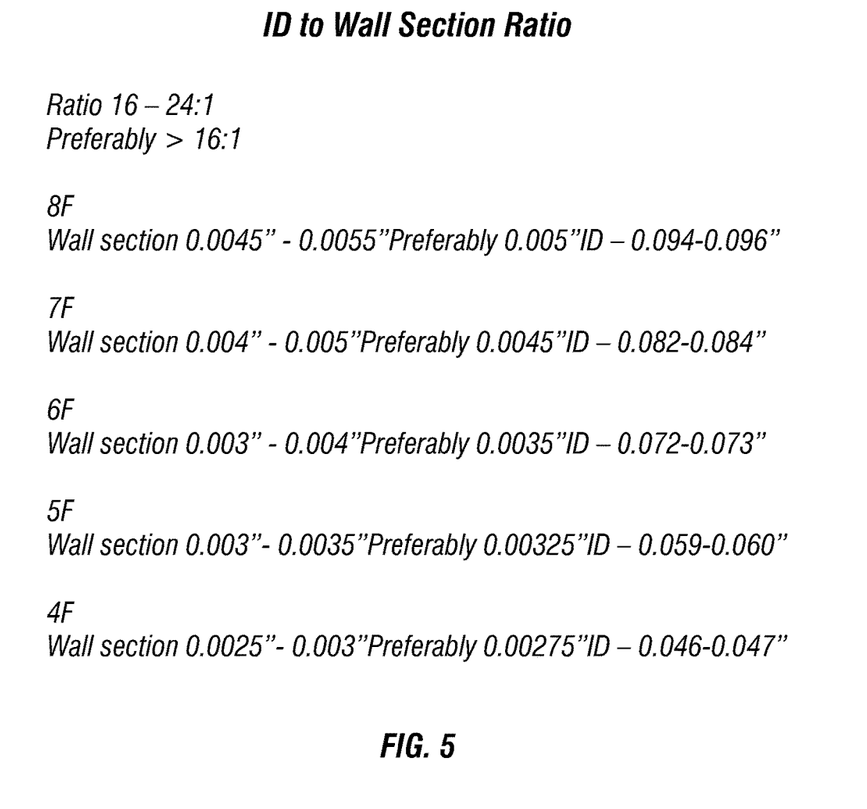
FIG. 5 is a table showing examples of inner diameter to wall thickness ratios for catheters 100, 100a of the present invention in sizes ranging from 4 French to 8 French.

FIG. 5 is a table showing examples of inner diameter to wall thickness ratios for catheters 100, 100a of the present invention in sizes ranging from 4 French to 8 French.

In some embodiments of the invention, an optional balloon, such as a compliant balloon formed of material such as latex, silicon, Chronoprene, Santoprene or other elastomers, may be positioned at or near the distal end of the elongate catheter body. Such optional balloon may be useful for occluding flow through the blood vessel in which the catheter is positioned when such flow occlusion is desired.

In at least some embodiments, the proximal section 101 will retain radial strength but provide lateral flexibility. Additionally, that section desirably has a lateral flexibility (Stiffness), such as would be measured by a Tinius-Olsen Stiffness Tester, of at least 1,200.degree. of deflection/inch-pound (measured at 20.degree.-30.degree. of deflection, 0.005 lb, over a 0.25" span), preferably 2,500.degree. of deflection/inch-pound. We have additionally found that the radial compression strength of the section is quite high as compared to other distal sections found on comparable catheter distal sections.

Access for the catheter of the present invention can be achieved using conventional techniques through an incision on a peripheral artery, such as right femoral artery, left femoral artery, right radial artery, left radial artery, right brachial artery, left brachial artery, right axillary artery, left axillary artery, right subclavian artery, or left subclavian artery. An incision can also be made on right carotid artery or left carotid artery in emergency situations.

The construction disclosed herein is suitable for guide catheter as a stand-alone device. This construction results in a highly flexible device having high column strength, torqueability, kink-resistance, and tensile strength.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless otherwise specified of if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims.

The invention claimed is:

1. A catheter device comprising:
an elongate tubular catheter body having a proximal end and a distal end and a passageway defining an inner lumen extending between those ends,
the elongate tubular catheter body comprising an inner tubular liner of a first liner material in coaxial relationship with an outer tubular cover, a tubular member between the inner tubular liner and the outer tubular cover, and a hydrophilic coating on an outer surface of the outer tubular cover, the tubular member comprising a metal helix defining a helical gap and a polymeric kink resistance member comprising a thermoset polymer positioned within the helical gap of the metal helix, and the catheter body, in the region of the distal end, having an inner diameter to wall thickness ratio greater than or equal to 16:1 and a kink radius of about 4.42 millimeters (mm)+/−0.203 mm (about 0.174 inch+/−0.008 inch) or less.

2. A guide catheter comprising:
an elongate tubular member having a proximal end and a distal end and a passageway defining an inner lumen extending between those ends, the elongate tubular member comprising:
   a) a relatively stiff proximal segment, the proximal segment comprising an inner proximal tubular liner comprising a proximal liner material in coaxial relationship with an outer proximal tubular cover comprising a proximal cover material, a metallic braid structure positioned upon the inner proximal tubular liner and covered by the outer proximal tubular cover;
   b) a relatively flexible distal segment, the distal segment comprising an inner distal tubular liner comprising a distal liner material in coaxial relationship with an outer distal tubular cover comprising a distal cover material, a distal tubular member between the distal liner material and the distal cover material, the distal tubular member comprising and a metal helix defining a helical gap and a polymeric kink resistance member structure positioned within the helical gap, the elongate tubular member, in the region of the distal end, having an inner diameter to wall thickness ratio greater than or equal to 16:1 and a kink radius of about 4.42 millimeters (mm)+/−0.203 mm (about 0.174 inch+/−0.008 inch) or less; and
   c) at least one intermediate segment defining a passageway between the relatively stiff proximal segment and the relatively flexible distal segment, the at least one intermediate segment providing a transition from the metallic braid structure to the distal tubular member.

3. A catheter device comprising:
a catheter body comprising:
   a tubular member having an inner lumen and an outer surface, said tubular member comprising a metal structure having a helical gap and a polymeric material disposed within the helical gap;
   an inner liner extending through the lumen of the tubular member and defining an inner lumen of the catheter; and
   an outer cover on the outer surface of the tubular member,
   wherein the polymeric material disposed within the helical gap is different from the materials of the inner liner and the outer cover, and
wherein a distal region of the catheter body has an inner diameter to wall thickness ratio greater than or equal to 16:1 and a kink radius of about 4.42 millimeters (mm)+/−0.203 mm (about 0.174 inch+/−0.008 inch) or less.

4. The catheter device of claim 3 wherein the distal region of the catheter body has an inner diameter to wall thickness ratio in a range of 16:1 to 24:1.

5. The catheter device of claim 3 wherein the distal region of the catheter body has a lateral flexibility of greater than or equal to 1200 degrees of deflection per pound-force inch.

6. The catheter device of claim 3 wherein the distal region of the catheter body has an Ultimate Tensile Strength of 22 Newtons.

7. The catheter device of claim 3, wherein the tubular member extends to a distal end of the catheter body.

8. The catheter device according to claim 3 wherein the metal structure comprises nickel titanium alloy.

9. The catheter device according to claim 3 wherein the metal structure comprises nickel titanium alloy ribbon.

10. The catheter device according to claim 3 wherein the metal structure is a metal helix having the helical gap.

11. The catheter device according to claim 10 wherein the helical gap is of continuous width.

12. The catheter device according to claim 10 wherein a dimension of the metal helix and/or width of the helical gap varies.

13. The catheter device according to claim 3 wherein the polymeric material comprises an elastomer.

14. The catheter device according to claim 3 wherein the polymeric material comprises a cast elastomer.

15. The catheter device according to claim 3 wherein the polymeric material comprises a cast polyurethane.

16. The catheter device according to claim 15 wherein the cast polyurethane comprises a thermoset polyurethane adhesive.

17. The catheter device according to claim 3 wherein the inner liner comprises at least one material selected from the group consisting of: fluoropolymers; PTFE; PFA; and FEP.

18. The catheter device according to claim 3 wherein the outer cover comprises at least one material selected from the group consisting of: polyesters and polyolefins.

19. The catheter device according to claim 10 wherein the catheter device has a plurality of regions along its length wherein a dimension of the metal helix and/or a width of the helical gap differ between said regions.

20. The catheter device according to claim 3 wherein the catheter device has a proximal region, a medial region and a distal region.

21. The catheter device according to claim 20 wherein the outer cover on the proximal region comprises polyester having a thickness of about 0.001 inch; the outer cover on the medial region comprises polyester having a thickness of about 0.0005 inch and the outer cover on the distal region comprises polyolefin having a thickness of about 0.0005 inch.

22. The catheter device according to claim 3 further comprising a balloon.

23. The catheter device according to claim 22 wherein the balloon comprises a compliant balloon.

24. The catheter device according to claim 3 wherein the polymeric material disposed within the helical gap is a thermoset polymer.

25. A method for manufacturing a catheter, the method comprising:
  forming a catheter body, wherein forming the catheter body comprises:
    A) forming or obtaining a metal helix defining a helical gap;
    B) disposing polymeric material comprising a thermoset polymer within the helical gap such that the polymeric material and the metal helix, in combination, form a tubular member having an outer surface and a lumen;
    C) disposing an inner liner within the lumen of the tubular member; and
    D) disposing an outer cover on the outer surface of the tubular member,
  wherein a distal region of the catheter body has an inner diameter to wall thickness ratio greater than or equal to 16:1 and a kink radius of about 4.42 millimeters (mm)+/−0.203 mm (about 0.174 inch+/−0.008 inch) or less.

26. The method according to claim 25 wherein disposing the inner liner within the lumen of the tubular member comprises disposing the inner liner on a mandrel and positioning the metal helix on top of the inner liner.

27. The method according to claim 26 wherein the metal helix comprises a nickel titanium alloy and disposing the inner liner within the lumen of the tubular member comprises winding the nickel titanium alloy about the inner liner and then heat setting the nickel titanium alloy.

28. The method according to claim 26 wherein disposing the inner liner within the lumen of the tubular member comprises casting a flowable polymer mixture into the helical gap and solidifying the flowable polymer, thereby forming the tubular member with the inner liner disposed therein.

29. The method according to claim 28 wherein the polymer comprises a polymer adhesive.

30. The method according to claim 29 further comprising applying a release agent or barrier to one or more selected areas of the metal helix to deter or interrupt adhesion of the polymer adhesive to the selected areas of the metal helix.

31. The method according to claim 29 wherein the polymer adhesive causes adhesion between the tubular member and the inner liner.

32. The method according to claim 29 further comprising disposing a quantity of the polymer adhesive between the outer surface of the tubular member and the inner surface of the outer cover to cause adhesion between the tubular member and the outer cover.

33. The method according to claim 25 wherein the outer cover comprises a tube that initially has an inner diameter that is larger than the outer diameter of the tubular member and wherein disposing the outer cover on the outer surface of the tubular member comprises advancing the outer cover over the tubular member and causing the outer cover to contact the outer surface of the tubular member.

34. The method according to claim 33 further comprising heat shrinking the outer cover onto the outer surface of the tubular member.

35. The method according to claim 25 further comprising disposing a radiographic marker on or in the catheter body.

36. The method according to claim 25 further comprising applying a hydrophilic coating to an outer surface of the outer cover.

37. A method for treating or diagnosing a disorder in a human or animal subject, said method comprising:
  inserting a catheter into the subject's vasculature, the catheter including:
    a tubular member having an inner lumen and an outer surface, said tubular member comprising a metal helix having a helical gap and a polymeric material disposed within the helical gap;
    an inner liner extending through the lumen of the tubular member and defining an inner lumen of the catheter; and
    an outer cover on the outer surface of the tubular member;
    wherein the polymeric material disposed within the helical gap is different from the materials of the inner liner and the outer cover and wherein a distal region of the catheter body has an inner diameter to wall thickness ratio greater than or equal to 16:1 and a kink radius of about 4.42 millimeters (mm)+/−0.203 mm (about 0.174 inch+/−0.008 inch or less);
  delivering a substance or device through the lumen of the catheter device; and
  using the substance or device to treat or diagnose the disorder.

38. The method according to claim 37 wherein inserting the catheter comprises advancing the catheter device into a blood vessel located within the subject's skull.

39. The method according to claim 38 further comprising selecting the blood vessel into which the catheter device is advanced from the group consisting of: carotid artery, cerebral artery, anterior cerebral artery, middle cerebral artery and posterior cerebral artery.

* * * * *